US007785868B2

(12) United States Patent
Yuan et al.

(10) Patent No.: US 7,785,868 B2
(45) Date of Patent: Aug. 31, 2010

(54) APPARATUS TO AUTOMATICALLY LYSE A SAMPLE

(75) Inventors: Bob Yuan, Belmont, CA (US); Allen Northrup, Orinda, CA (US); Farzad Pourahmadi, Fremont, CA (US)

(73) Assignee: Microfluidic Systems, Inc., Fremont, CA (US)

( * ) Notice: Subject to any disclaimer, the term of this patent is extended or adjusted under 35 U.S.C. 154(b) by 1262 days.

(21) Appl. No.: 11/290,653

(22) Filed: Nov. 29, 2005

(65) Prior Publication Data

US 2006/0121603 A1 Jun. 8, 2006

Related U.S. Application Data

(60) Provisional application No. 60/633,037, filed on Dec. 2, 2004.

(51) Int. Cl.
*C12M 1/42* (2006.01)
(52) U.S. Cl. .............. 435/306.1; 435/286.7; 435/303.3; 241/2; 366/114; 366/127
(58) Field of Classification Search ................ 435/259, 435/286.7, 303.3, 306.1; 241/2; 366/114, 366/127; 134/107, 901; 310/325
See application file for complete search history.

(56) References Cited

U.S. PATENT DOCUMENTS

| | | | | |
|---|---|---|---|---|
| 3,720,402 | A | * | 3/1973 | Cummins et al. ........... 366/114 |
| 3,735,159 | A | * | 5/1973 | Murry ........................ 310/325 |
| 3,851,861 | A | * | 12/1974 | Cummins et al. ........... 366/114 |
| 4,275,166 | A | | 6/1981 | McCollough et al. ....... 435/227 |
| 4,666,595 | A | | 5/1987 | Graham ...................... 210/222 |
| 5,048,520 | A | | 9/1991 | Vago ......................... 128/24 A |
| 5,074,474 | A | * | 12/1991 | Golz et al. .................... 241/1 |
| 5,234,809 | A | | 8/1993 | Boom et al. ................... 435/91 |
| 5,475,203 | A | | 12/1995 | McGaffigan ................ 219/548 |
| 5,707,799 | A | | 1/1998 | Hansmann et al. ............. 435/6 |
| 5,952,173 | A | | 9/1999 | Hansmann et al. ............. 435/6 |

(Continued)

FOREIGN PATENT DOCUMENTS

WO    WO 99/33559 A1    7/1999

(Continued)

OTHER PUBLICATIONS

"High Sensitivity PCR Assay in Plastic Micro Reactors", Jianing Yang et al., Physical Sciences Research Laboratories, Motorola Labs, Motorola, Inc., 7700 S. River Parkway, MD-ML34, Tempe, AZ 85284, USA, Revised Aug. 29, 2002, pp. 179-187.

(Continued)

*Primary Examiner*—William H Beisner
(74) *Attorney, Agent, or Firm*—Haverstock & Owens LLP

(57) ABSTRACT

A standalone bench top laboratory instrument designed to disrupt, or lyse, cells, spores and tissue samples using ultrasonic energy. The lysing device is programmable, allowing the user control over the sample volume, sonication power level, and lysing duration in order to optimize lysing protocols for specific targets. Once a lysing protocol is entered, the device automatically lyses the sample according to the entered lysing protocol. The lysing device also provides a cooling feature, enabled by a heat exchanging sub-assembly, to prevent the sample from exceeding a maximum set temperature.

35 Claims, 5 Drawing Sheets

U.S. PATENT DOCUMENTS

| | | | |
|---|---|---|---|
| 6,033,880 A | 3/2000 | Haff et al. | 435/91.1 |
| 6,087,183 A | 7/2000 | Zaromb | 436/178 |
| 6,100,084 A | 8/2000 | Miles et al. | 435/306.1 |
| 6,228,634 B1 | 5/2001 | Blumenfeld et al. | 435/286.1 |
| 6,318,158 B1* | 11/2001 | Breen et al. | 73/64.56 |
| 6,374,684 B1* | 4/2002 | Dority | 73/864.81 |
| 6,391,541 B1* | 5/2002 | Petersen et al. | 435/5 |
| 6,565,815 B1* | 5/2003 | Chang et al. | 422/198 |
| 6,578,659 B2* | 6/2003 | Manna et al. | 181/142 |
| 6,741,174 B2 | 5/2004 | Rhoades et al. | 340/540 |
| 6,818,185 B1 | 11/2004 | Petersen et al. | |
| 6,977,145 B2 | 12/2005 | Fouillet et al. | 435/6 |
| 7,005,982 B1 | 2/2006 | Frank | 340/539.26 |
| 7,006,923 B1 | 2/2006 | Rubin | 702/19 |
| 7,082,369 B1 | 7/2006 | Rubin et al. | 702/19 |
| 7,106,442 B2 | 9/2006 | Silcott et al. | 356/338 |
| 7,228,067 B2 | 6/2007 | Magni et al. | 392/480 |
| 7,411,792 B2 | 8/2008 | Richards et al. | |
| 7,491,527 B2 | 2/2009 | Yuan et al. | |
| 2001/0032666 A1 | 10/2001 | Jenson et al. | 136/256 |
| 2001/0036630 A1 | 11/2001 | Ibrahim | 435/6 |
| 2002/0022261 A1 | 2/2002 | Anderson et al. | 435/287.2 |
| 2002/0039783 A1 | 4/2002 | McMillan et al. | 435/287.2 |
| 2002/0142482 A1 | 10/2002 | Wu et al. | 436/177 |
| 2002/0187547 A1* | 12/2002 | Taylor et al. | 435/306.1 |
| 2003/0038087 A1 | 2/2003 | Garvin | 210/767 |
| 2003/0073229 A1 | 4/2003 | Greenstein et al. | 435/287.2 |
| 2003/0215845 A1 | 11/2003 | Bille | 435/6 |
| 2004/0197793 A1 | 10/2004 | Hassibi et al. | 435/6 |
| 2005/0064598 A1 | 3/2005 | Yuan et al. | 436/63 |
| 2005/0142565 A1 | 6/2005 | Samper et al. | 435/6 |
| 2005/0227275 A1 | 10/2005 | Jung et al. | 435/6 |
| 2006/0079000 A1 | 4/2006 | Floriano et al. | 436/164 |
| 2007/0116607 A1 | 5/2007 | Wang et al. | 422/83 |
| 2008/0050803 A1 | 2/2008 | Northrup et al. | 435/287.2 |

FOREIGN PATENT DOCUMENTS

| | | |
|---|---|---|
| WO | WO 03/070898 A2 | 8/2003 |

OTHER PUBLICATIONS

Office Action dated May 26, 2009, U.S. Appl. No. 11/509,872, 15 pages.

Office Action mailed Aug. 6, 2009. U.S. Appl. No. 11/352,108, filed Feb. 9, 2006, Applicant; Phillip I. Belgrader, 8 pages.

International Search Report including the Written Opinion for International Application No.: PCT/US09/62068, International Filing Date Oct. 26, 2009, 9 pages.

* cited by examiner

APPARATUS TO AUTOMATICALLY LYSE A SAMPLE

RELATED APPLICATIONS

This application claims priority of U.S. provisional application, Ser. No. 60/633,037, filed Dec. 2, 2004, and entitled "An Autolysing Device", by the same inventors. This application incorporates U.S. provisional application, Ser. No. 60/633,037 in its entirety by reference.

FIELD OF THE INVENTION

The present invention relates to a method of and an apparatus for automatically lysing a sample. In particular, the present invention relates to a method of and an apparatus for automatically lysing a sample using ultrasonic energy.

BACKGROUND OF THE INVENTION

Current lysing techniques use heat, chemicals, mechanical grinding/bombardment or a combination of these to achieve cell/spore/tissue disruption.

Methods that rely on chemical or heat lysis alone often require a number of manual steps that the user must strictly follow. If chemicals are used for lysing, often the lysing protocol will require that chemical additives be neutralized after lysing to prevent inhibition in later analyses. This adds complexity, time, and cost to the process.

Mechanical grinding methods, such as using a mortar and pestle, are also manual in nature and thus their effectiveness and repeatability are dependent on the skill of the technician. The additional step of cleaning all of the instruments after each test is required to eliminate the risk of cross contamination between samples.

Current devices that use ultrasonic energy for mechanical lysing require the transducer tip be immersed into the liquid sample during sonication, which again presents the risk of cross contamination between samples if the transducer tip is not thoroughly cleaned between tests. Also, accessibility of the liquid sample to introduce the transducer tip necessitates that the liquid sample be contained in an open environment. Such an open environment increases the possibility of contamination via splashing or atomization.

Another method of mechanical disruption is called the "Bead Beater," where the sample is put into a container together with rigid beads (e.g. glass or stainless steel spheres). The container is then violently shaken for a set amount of time in a manner similar to a paint mixer. This method is similar in principle to using ultrasonic energy for mechanical disruption, but with a lower frequency and higher amplitude of shaking. Cross contamination between tests is not an issue if new containers are used for each sample, otherwise, the container must be thoroughly cleaned before each new test. However, for some samples, a higher level of agitation is required.

It would be advantageous to develop a lysing system and method that is more automated, more efficient, and less prone to contamination.

SUMMARY OF THE INVENTION

Embodiments of the present invention are directed to a standalone bench top laboratory instrument designed to disrupt, or lyse, cells, spores and tissue samples using ultrasonic energy. The lysing device is programmable, allowing the user control over lysing protocol parameters, such as the sample volume, sonication power level, and lysing duration. Such programmable control enables optimizing protocols for specific targets. Once a lysing protocol is entered, the device automatically lyses the sample according to the entered lysing protocol. The lysing device also provides a cooling feature, enabled by a heat exchanging sub-assembly, which prevents the sample from exceeding a maximum set temperature during operation. During certain lysing protocols, temperatures can increase to a point that are potentially destructive to particular samples. In these cases, the heat exchanging sub-assembly can be used to transfer heat away from the sample.

The lysing system of the present invention preferably utilizes a disposable, individually capped sample vial for each sample to be lysed, minimizing the risk of cross contamination between tests. The sample can be combined with mechanical agitation media (e.g. glass spheres), chemical lysing reagents (e.g. NaOH), other conventional lysing techniques, or nothing depending on the lysing protocol. A sample vial holding the sample is inserted into the lysing device such that the bottom of the sample vial comes in contact with the transducer tip of the ultrasonic transducer. The transducer tip does not come in contact with the sample. The sample vial is inserted into a vial mount within the lysing device. Heat blocks are pressed tightly against the side walls of the sample vial. The heat blocks are each mounted to a Thermoelectric Cooler (TEC) and heatsink. The ultrasonic transducer transmits ultrasonic energy through the bottom of the sample vial and into the sample to cause cell/spore/tissue disruption. When the cooling function is activated, the TECs actively cool the sample by pulling heat from the sample vial via the heat blocks. Preferably an auxiliary fan blows across the TECs and heatsinks to maintain the heat removal rate.

DETAILED DESCRIPTION OF THE PRESENT INVENTION

Figure 1:
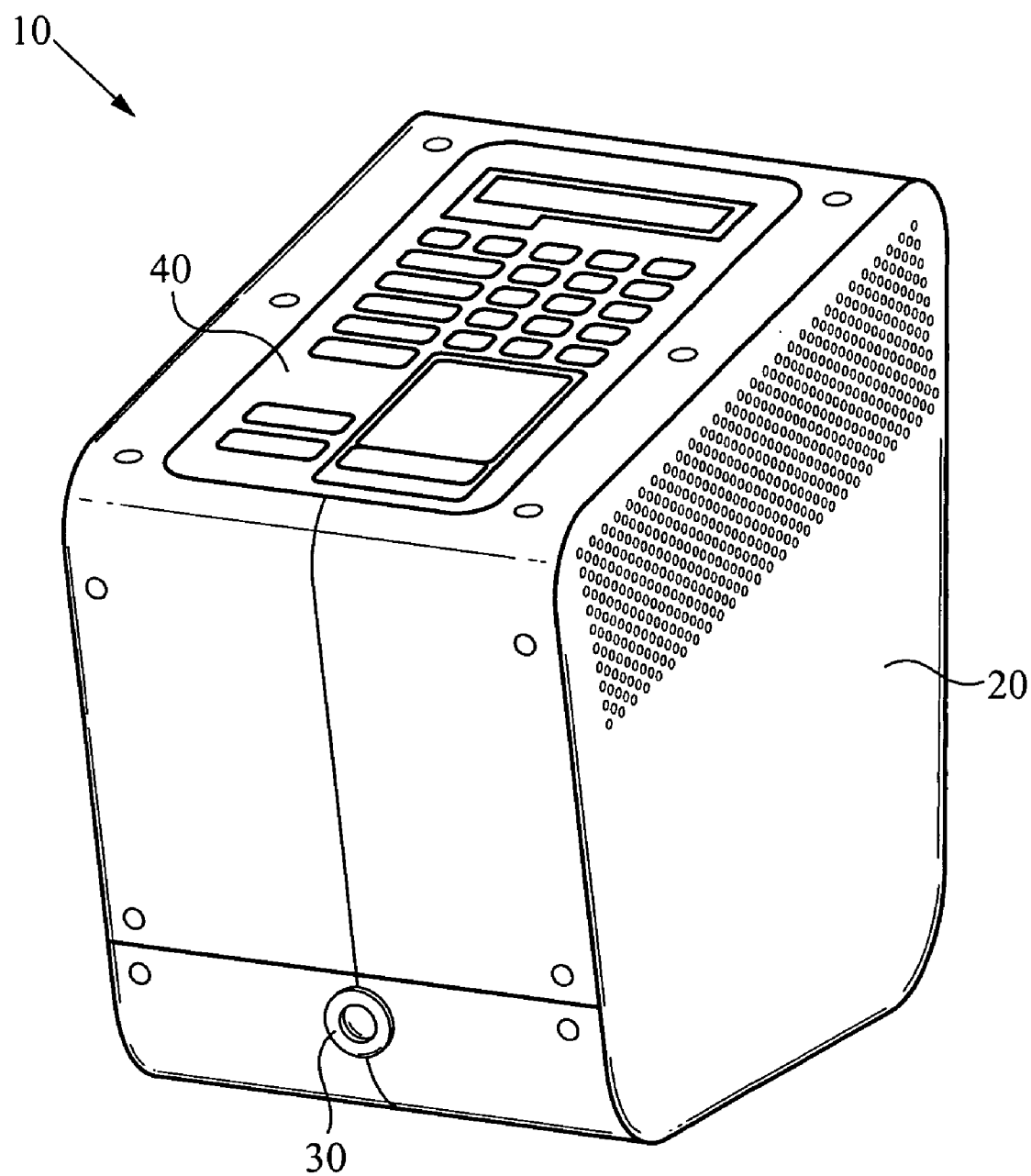
FIG. 1 illustrates a perspective view of an automatic lysing device according to the preferred embodiment of the present invention.

FIG. 1 illustrates a perspective view of an automatic lysing device 10 according to a preferred embodiment of the present invention. The lysing device 10 includes a housing 20, a main power switch 30, and a control panel 40.

Figure 2:
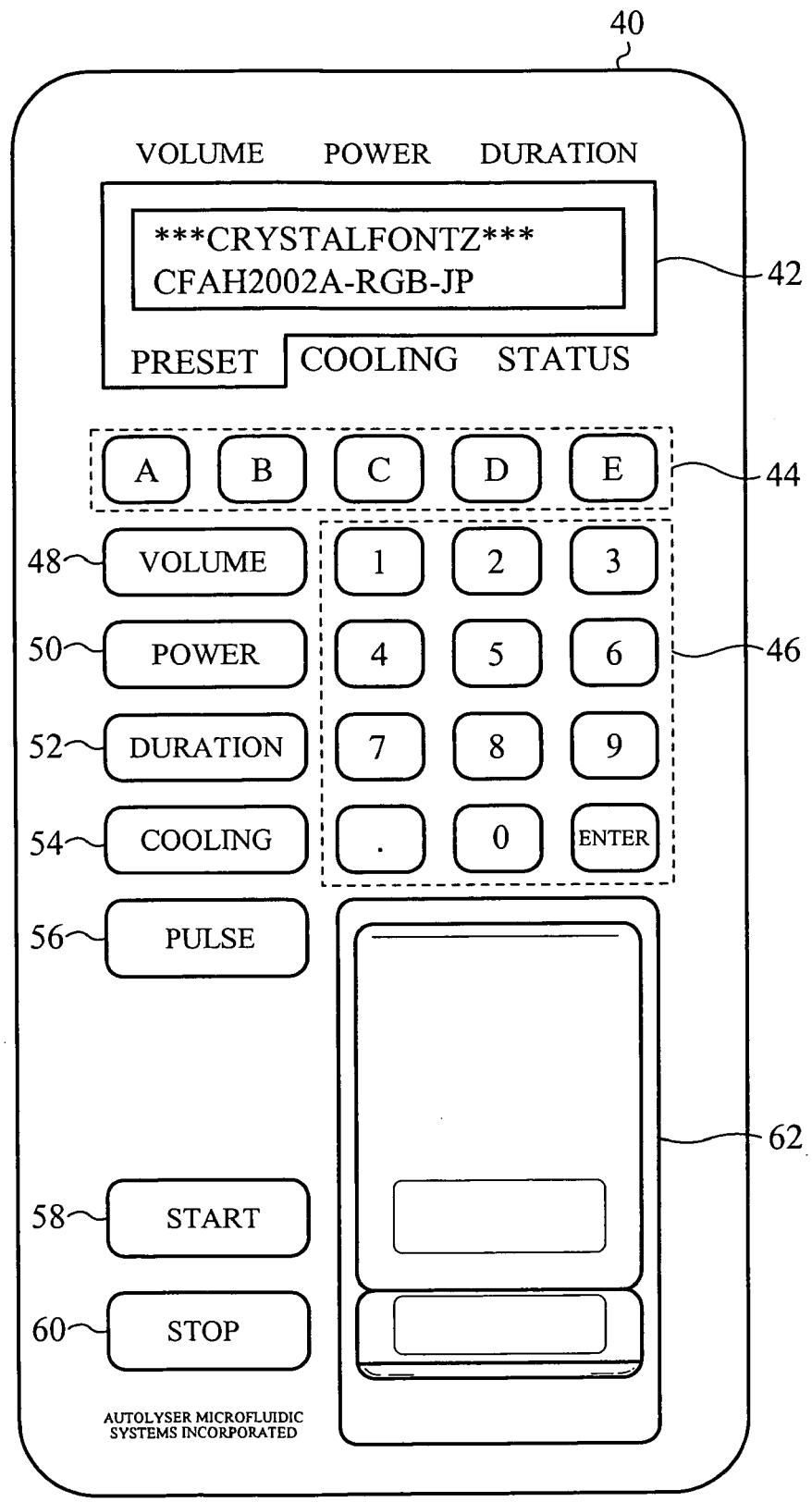
FIG. 2 illustrates a top down view of the control panel of the lysing device.

FIG. 2 illustrates the control panel 40 in greater detail. The control panel 40 is a user interface that enables a user to input various lysing protocol parameters. A visual display 42 displays the input parameters as well as feedback and status information during operation. The display 42 is preferably a liquid crystal display (LCD). Alternatively, any conventional display device is used. Less desirably, a printer such as a paper tape printer, can be used. A volume button 48, a power button 50, a duration button 52, and a cooling button 54 enable the user to enter a volume parameter, a power parameter, a duration parameter, and a cooling parameter, respectively. A numeric keypad 46 enables the user to enter numeric values associated with the volume, power, duration, and cooling parameters. The lysing device 10 (FIG. 1) is preferably configured to lyse sample volumes in the range of about 1.0 mL to about 3.0 mL Alternatively, the lysing device 10 is configured to accept sample volumes less than 1.0 mL and greater than 3.0 mL. The volume parameter is preferably entered in 0.1 mL increments. Alternatively, the volume parameter is entered in smaller or larger increments as required. In a further alternate embodiment, the user can also provide the type of power to which the actual wattage figures refer.

In the preferred embodiment, the power parameter is set according to one of five available power settings. The power settings are numbered from "1" to "5" with "1" being the lowest power. Alternatively, more or less than five power levels are configured. Power level settings are used instead of actual wattage figures, such as "10 watts", in order to avoid possible user confusion. For example, when inputting a specific wattage level, it may be unclear as to whether the input wattage level refers to power delivered by the power supply, power delivered by the ultrasonic transducer, or power absorbed into the sample. In an alternative embodiment, the system is configured to accept actual wattage figures for the power parameter. In a further alternate embodiment, the user can also provide the type of power to which the actual wattage figures refer.

The duration parameter corresponds to the amount of time that ultrasonic energy is to be applied to the sample, also referred to as lysing time. Preferably the lysing time is entered in minutes and seconds.

In general, the various combinations of possible volume, power, and duration parameter values collectively result in a performance envelope. The lysing device 10 is configured such that the instrument does not allow the user to run a lysing protocol with parameters that do not fall within known, or predefined, combination levels. Such a constraint prevents potential hazardous parameters combinations from being executed, for example running a very small volume at a very high power. In this manner, the potential for damaging the equipment and/or the sample is reduced. When parameter values are input that do not fall within the predefined performance envelope, an error message is displayed on the display 42, and the user is prompted to change one or more of the parameter values. Although the lysing device 10 is described as using the volume parameter, the power parameter, the duration parameter, and the cooling parameter, it is understood that more, or less, parameters can be used.

Once acceptable volume, power and duration parameters are set, a start button 58 is pressed and lysing begins. The display 42 shows elapsed time counting down to zero, as well as the set volume and power parameters. Operation is halted at any time by pressing a stop button 60.

In some cases, the lysing protocol, and corresponding parameter values, is not known and a new protocol needs to be developed. When developing a new protocol, the exact lysing duration may not yet be known and the user must instead manually control the timing. A pulse button 56 enables the user to manually lyse the sample at the set volume and power level. Ultrasonic energy is applied to the sample vial as long as the pulse button 56 is depressed, and the display 42 shows the elapsed pulse time by counting up. In the preferred embodiment, internal sensors continually monitor the temperature of the sample. If the pulse button 56 is held down for too long, overheating may result. Temperature thresholds are preferably defined such that if the temperature rises above a given threshold, application of the ultrasonic energy is halted.

Memory preset buttons 44 are provided such that commonly used protocols are stored and accessed with a single button press. Preferably, five preset buttons 44, A through E, are provided. Alternatively, more or less than five preset buttons can be configured.

The lysing device 10 includes the ability to cool the sample. The cooling parameter is preferably used to set a specific temperature to which the sample is cooled. Alternatively, the cooling parameter sets a target temperature range. Still alternatively, the cooling parameter is set to either on or off, with no specific temperature target set. Such a cooling feature is useful with certain protocols where the heat from sonication is undesirable, such as damaging RNA or reducing the rate of blood coagulation. The ability to cool the sample during sonication or pre-cool the sample prior to sonication also enables the application of longer duration lysing without overheating the sample or the sample vial.

The control panel 40 also includes an access lid 62. The access lid 62 provides the user access to a sample holding area, referred to as a vial mount 110 (FIG. 5), where a sample container, such as the sample vial, is placed for execution of a lysing protocol.

Figure 3:
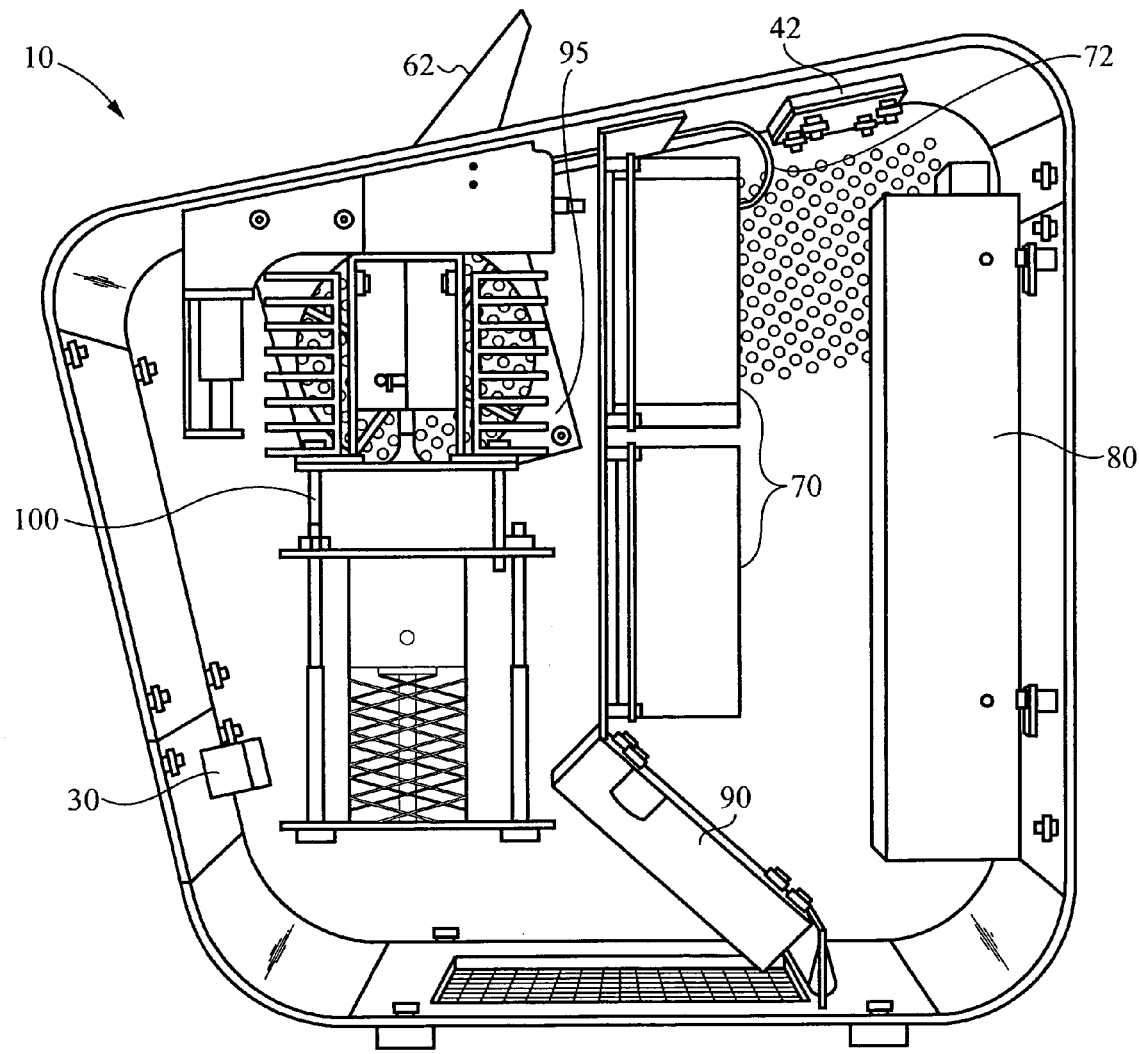
FIG. 3 illustrates an internal side view of the lysing device.

FIG. 3 illustrates an internal side view of the lysing device 10. The lysing device 10 includes two compartments, a lysing engine compartment and an electronics compartment. The lysing engine compartment includes a lysing engine 100. The electronics compartment includes control electronics 70, a power supply 80, and an electronics cooling fan 90. The control electronics 70 are coupled to the control panel 40 (FIG. 2) via connection 72. Configuring the lysing device 10 into the lysing engine compartment and the electronics compartment provides thermal isolation and fluid/electrical isolation. Thermal isolation keeps heat generated during sonication within the lysing engine 100 from heating the control electronics 70 within the electronics compartment, and keeps heat generated by the control electronics 70 and the power supply 80 from heating the lysing engine 100. Fluid/electrical isolation keeps fluids, such as the sample, cleaning agents, and TEC condensation away from sensitive electrical components within the control electronics 70.

Figure 4:
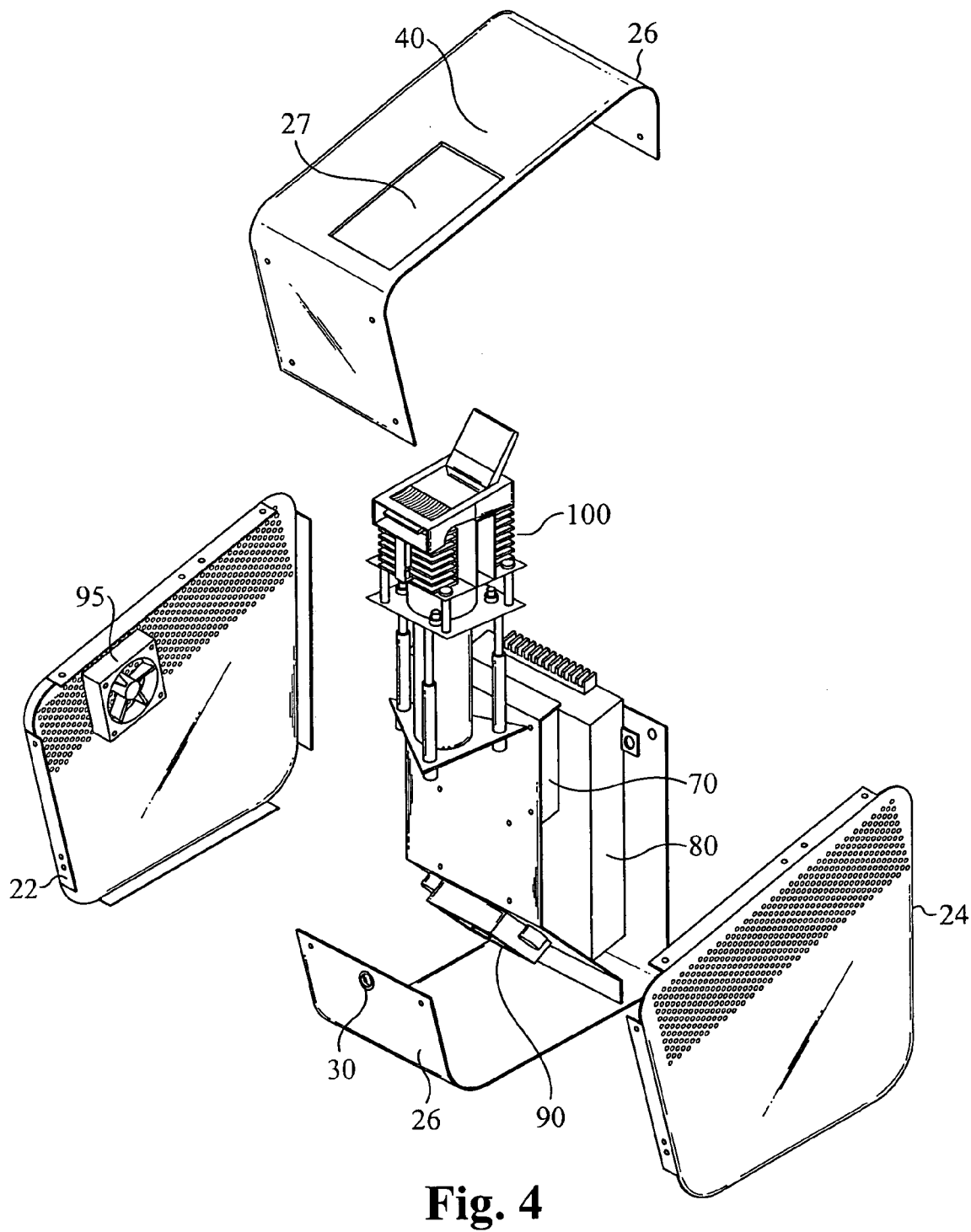
FIG. 4 illustrates an exploded view of the lysing device.

FIG. 4 illustrates an exploded view of the lysing device 10. The housing 20 (FIG. 1) preferably includes side panels 22 and 24, top cover 26, and bottom panel 26. Each of the side panels 22 and 24 are preferably perforated for venting. Attached to at least one of the side panels 22 and 24 is an auxiliary TEC fan 95. The auxiliary TEC fan 95 blows air drawn through the perforated vents of the housing past the lysing engine 100 for cooling. The top cover 26 includes the control panel 40 and an opening 27. A top portion of the lysing engine 100 protrudes through the opening 27 to provide the user access via the access lid 62. Although the housing 20 is illustrated in FIG. 4 as comprising 4 pieces, the housing 20 can alternatively comprise any number of component pieces.

Figure 5:
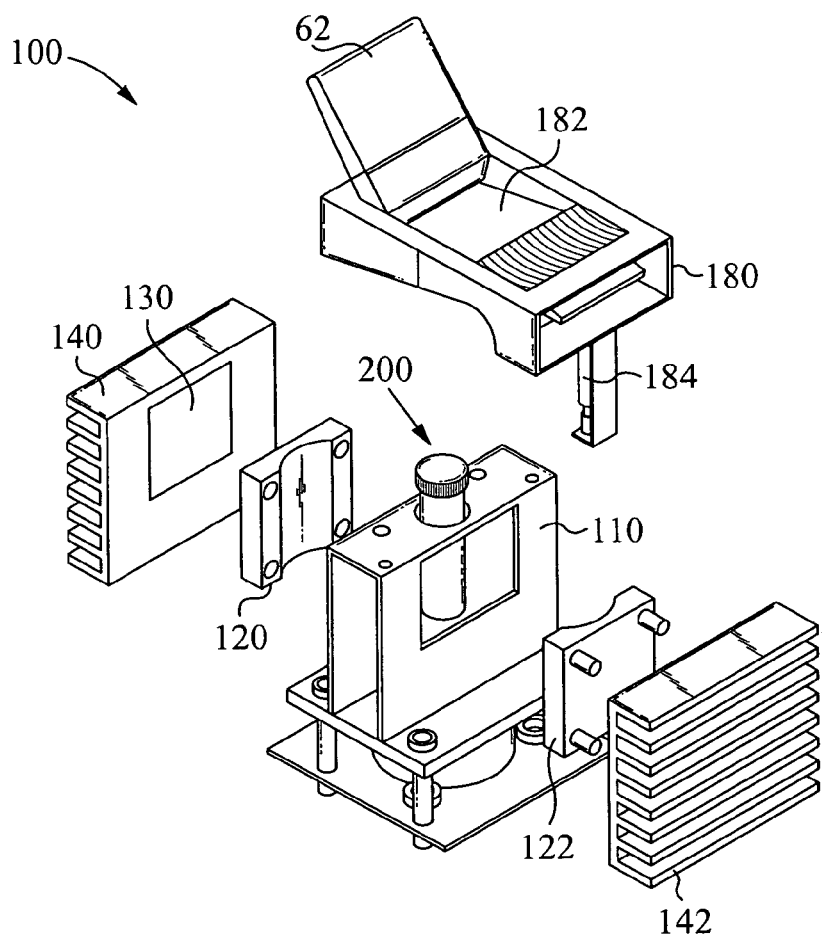
FIG. 5 illustrates an exploded view of the lysing engine.
Figure 5:
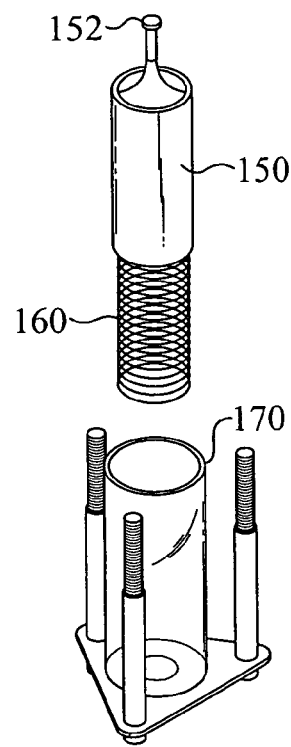

An exploded view of the lysing engine 100 is illustrated in FIG. 5. The lysing engine 100 includes a vial nest 180, a vial mount 110, heat blocks 120 and 122, thermoelectric coolers (TECs) 130, heat sinks 140 and 142, ultrasonic transducer 150, compression spring 160, and transducer mount 170. The vial nest 180 includes a release latch (not shown) and the access lid 62. The top portion of the vial nest 180, including the release latch and the access lid 62, protrudes through the opening 27 (FIG. 4) of the top cover 26 (FIG. 4).

The vial mount 110 is configured to hold a sample vial 200. When the access lid 62 is open, an access opening 182 in the vial nest 180 provides access to the vial mount 110. The sample vial 200 is placed into or removed from the vial mount 110 through the access opening 182.

A bottom portion of the ultrasonic transducer 150 is coupled to the compression spring 160. The transducer mount 170 holds and axially guides the ultrasonic transducer 150 and the compression spring 160 in place relative to each other. The transducer mount 170 is mounted to a bottom surface of the vial mount 110. In this manner, the ultrasonic transducer 150 is properly positioned relative to the vial mount 110. The vial mount 110 is preferably configured with an opening (not shown) in the bottom surface such that a transducer tip 152 of the ultrasonic transducer 150 passes through the opening and contacts a bottom surface of the sample vial 200 placed within the vial mount 110.

The sample vial 200 is placed into the vial mount 110. Subsequent closing of the access lid 62 compresses the bottom of the sample vial 200 against the transducer tip 152. A predetermined force is maintained by the transducer tip 152 against the bottom of the sample vial 200 by the calibrated compression spring 160. Efficient transfer of the ultrasonic energy from the ultrasonic transducer 150 to the sample within the sample vial 200 is dependent in part upon maintaining the contact between the transducer tip 152 and the bottom of the sample vial 200 according to the predetermined force. Maintaining proper predetermined force also plays a role in proper execution of any given lysing protocol, as the power parameter is a key variable in such calculations.

Although the compression spring 160 preferably maintains a substantially constant force of the transducer tip 152 against the bottom of the sample vial 200, the coupling that occurs at this interface changes during lysing due to heating of the interface and slight positional changes due to the mechanical movement. To compensate for this drift and maintain the set input power level, a feedback loop circuit is preferably incorporated into the control electronics 70 that control the ultrasonic transducer 150. The feedback circuit preferably samples the voltage and current fed to the ultrasonic transducer 150, and computes the power delivered to the transducer tip 152 in real time, preferably ever 10 msec. The control electronics 70 then adjust the supply voltage internal to a voltage controller of the ultrasonic transducer 150, which changes the drive voltage to the ultrasonic transducer 150. The impedance of the ultrasonic transducer 150 and the voltage drive level then determines the current drawn.

When the sample vial 200 is positioned in the vial mount 110, two spring-loaded heat blocks 120 and 122 press against the sides of the sample vial 200. In this manner, a first surface of each of the heat blocks 120 and 122 is in contact with the sample vial 200 to provide a thermal contact for heat transfer. A second surface of each of the heat blocks 120 and 122 is preferably in contact with the Thermoelectric Cooler (TEC) 130. Although not shown in FIG. 5 due to the angle of perspective, a second TEC is mounted on a back side of the heat sink 142 in a manner similar to the first TEC 130. The TEC 130 and the second TEC (not shown) are preferably mounted to a back side of the heat sink 140 and the heat sink 142, respectively. A "hot" side of each TEC is mounted to the heat sinks 140 and 142. When the cooling function is activated, the TECs are energized causing one side to get cold (below the ambient air temperature) and the other side to get hotter then the ambient. The cold sides of each TEC, mounted to the heat blocks 120 and 122, extract heat generated from the sample during application of the ultrasonic energy sonication. The auxiliary TEC fan 95 (FIG. 4) cools the heat sinks 140 and 142 to maintain a temperature gradient across the TECs necessary for proper operation.

A temperature sensor (not shown) is preferably mounted to at least one of the heat blocks 120 and 122 to monitor the temperature. This temperature is directly correlated to the temperature of the sample vial 200 and the sample within. Maintaining the temperature within a predetermined range expands lysing protocol capability. Additionally, measuring the temperature, and by extension using the cooling feature of the lysing device 10, is used for a variety of safeguard functions. When the lysing device 10 senses potential overheating, the sonication process is automatically stopped or reduced. If the cooling parameter was not previously turned on, the TECs are activated at this time, rapidly cooling the sample vial 200 and the sample within to a safe temperature.

During normal operation of the lysing device 10, it is expected that the sample will experience some heating, which often enhances lysing. Although not high enough to present a risk of vial rupture or damage to the target, these temperatures may be high enough to startle, or mildly burn, the user if the sample vial 200 is removed from the instrument and handled (e.g. risk of dropping the vial and inadvertent spillage). To minimize such a risk, the lysing device 10 includes a solenoid safety interlock 184, which disables the release latch, to prevent the user from releasing the access lid 62 and accessing the sample vial 200 before it has cooled down to a safe temperature. Momentarily activating the TECs after completion of the lysing protocol rapidly cools the sample vial 200 and the sample within to a "safe" temperature, and shortens the period waiting for the safety interlock 184 to release the access lid 62.

Lysing effectiveness has been shown using *Bacillus Globigii* (*BG*) bacteria spores. 3 mL samples with $10^4$ cfu/mL concentration of *BG* combined with 240 mg of glass beads (150-212 micron diameter) have been sonicated at power level two for 10 minutes and then amplified using PCR showing successful lysing had occurred. Preferably, power level two is equivalent to delivering 8 watts directly to the sample.

The lysing engine 100 is preferably designed as an individual subassembly. As such, the lysing engine 100 can alternatively be used, with little or no changes, for alternative instrument configurations. Such alternative instrument configurations including ganging together lysing engine sub-assemblies in multi-station systems, or combining a lysing engine sub-assembly with other devices into a single instrument.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. An apparatus to control temperature while lysing a sample using ultrasonic energy, the apparatus comprising:
   a. a sample container to hold the sample to be lysed;
   b. an ultrasonic generator in contact with the sample container to provide ultrasonic energy to the sample;
   c. a heat exchanging sub-assembly coupled to the sample container, wherein the heat exchanging sub-assembly includes at least one spring-loaded heat block that is pressed into contact with the sample container, a heat sink, and a thermoelectric cooler thermally coupled between the at least one heat block and the heat sink, further wherein the heat exchanging sub-assembly is configured such that heat generated within the sample container during application of the ultrasonic energy is transferred from the sample container to the heat exchanging sub-assembly.

2. The apparatus of claim 1 wherein the ultrasonic generator comprises a sonication horn.

3. The apparatus of claim 2 wherein the sonication horn includes a transducer tip, further wherein the transducer tip is positioned to contact a first surface of the sample container.

4. The apparatus of claim 3 further comprising a compression spring coupled to the sonication horn, wherein the compression spring is calibrated such that a predetermined force is maintained by the transducer tip against the first surface of the sample container.

5. The apparatus of claim 3 wherein the sample container is sealed and the transducer tip contacts an external surface of the sample container, thereby providing a sealed environment within the sample container.

6. The apparatus of claim 1 wherein the ultrasonic energy lyses a cell, a spore, or a tissue within the sample.

7. The apparatus of claim 1 further comprising a variable programming circuit coupled to the ultrasonic generator to control a power and a duration of the ultrasonic energy applied.

8. The apparatus of claim 7 wherein the apparatus is partitioned into a lysing engine compartment and an electronics compartment that are thermally isolated from each other, wherein the sample container, the ultrasonic generator, and the heat exchanging sub-assembly are positioned in the lysing engine compartment, and the variable programming circuit is positioned in the electronics compartment such that the variable programming circuit is thermally isolated from the sample container, the ultrasonic generator, and the heat exchanging sub-assembly.

9. The apparatus of claim 7 further comprising a temperature sensor coupled to the heat exchanging sub-assembly.

10. The apparatus of claim 9 wherein the variable programming circuit is coupled to the temperature sensor to receive temperature information, further wherein the variable programming circuit provides control signals to the ultrasonic generator in response to the temperature information.

11. The apparatus of claim 7 further comprising a user interface coupled to the variable programming circuit, the user interface is used to enter operation parameters.

12. The apparatus of claim 11 wherein the operation parameters include a volume size of the sample, a power level of the ultrasonic energy to be applied, and a duration for which the ultrasonic energy is to be applied.

13. The apparatus of claim 1 wherein the sample container is removable from the apparatus.

14. An apparatus to lyse a sample using ultrasonic energy, the apparatus comprising:
  a. a sample container to hold the sample to be lysed;
  b. an ultrasonic generator in contact with the sample container to provide ultrasonic energy to the sample;
  c. a heat exchanging sub-assembly coupled to the sample container to facilitate heat transfer to and from the sample container, wherein the heat exchanging sub-assembly includes at least one spring-loaded heat block that is pressed into contact with the sample container;
  d. a variable programming circuit to provide control signals to the ultrasonic generator according to a provided lysing protocol.

15. The apparatus of claim 14 wherein the ultrasonic generator comprises a sonication horn.

16. The apparatus of claim 15 wherein the sonication horn includes a transducer tip, further wherein the transducer tip is positioned to contact a first surface of the sample container.

17. The apparatus of claim 16 further comprising a compression spring coupled to the sonication horn, wherein the compression spring is calibrated such that a predetermined force is maintained by the transducer tip against the first surface of the sample container.

18. The apparatus of claim 16 wherein the sample container is sealed and the transducer tip contacts an external surface of the sample container, thereby providing a sealed environment within the sample container.

19. The apparatus of claim 14 wherein the heat exchanging sub-assembly further comprises a thermoelectric cooler coupled to the at least one heat block.

20. The apparatus of claim 14 wherein the ultrasonic energy lyses a cell, a spore, or a tissue within the sample.

21. The apparatus of claim 14 wherein the lysing protocol specifies a power level of the ultrasonic energy, a duration for which the ultrasonic energy is to be applied, or a volume size of the sample included within the sample container.

22. The apparatus of claim 21 further comprising a user interface coupled to the variable programming circuit, the user interface is used to enter the lysing protocol.

23. The apparatus of claim 14 further comprising a temperature sensor coupled to the heat exchanging sub-assembly.

24. The apparatus of claim 23 wherein the variable programming circuit is coupled to the temperature sensor to receive temperature information, further wherein the variable programming circuit provides control signals to the ultrasonic generator in response to the temperature information.

25. An apparatus to lyse a sample using ultrasonic energy, the apparatus comprising:
  a. a sample stored within a sealed environment;
  b. a sonication horn positioned to contact an external surface of the sealed environment, wherein the sonication horn generates ultrasonic energy which is provided to the sample via the external surface; and
  c. a heat exchanging sub-assembly coupled to the sealed environment to facilitate heat transfer to and from the sealed environment, wherein the heat exchanging sub-assembly includes at least one spring-loaded heat block that is pressed into contact with the sealed environment.

26. The apparatus of claim 25 wherein the sonication horn includes a transducer tip, further wherein the transducer tip is positioned to contact the external surface of the sealed environment.

27. The apparatus of claim 26 further comprising a compression spring coupled to the sonication horn, wherein the compression spring is calibrated such that a predetermined force is maintained by the transducer tip against the external surface of the sealed environment.

28. The apparatus of claim 25 wherein the sealed environment comprises a vial with a cap.

29. The apparatus of claim 25 wherein the heat exchanging sub-assembly further comprises a thermoelectric cooler coupled to the at least one heat block.

30. The apparatus of claim 25 wherein the ultrasonic energy lyses a cell, a spore, or a tissue within the sample.

31. The apparatus of claim 25 further comprising a variable programming circuit coupled to the ultrasonic generator to control a power and a duration of the ultrasonic energy applied.

32. The apparatus of claim 31 further comprising a temperature sensor coupled to the heat exchanging sub-assembly.

33. The apparatus of claim 32 wherein the variable programming circuit is coupled to the temperature sensor to receive temperature information, further wherein the variable programming circuit provides control signals to the ultrasonic generator in response to the temperature information.

34. The apparatus of claim 31 further comprising a user interface coupled to the variable programming circuit, the user interface is used to enter operation parameters.

35. The apparatus of claim 34 wherein the operation parameters include a volume size of the sample, a power level of the ultrasonic energy to be applied, and a duration for which the ultrasonic energy is to be applied.

* * * * *